(12) United States Patent
Rowe et al.

(10) Patent No.: US 8,173,120 B2
(45) Date of Patent: May 8, 2012

(54) METHOD OF PREVENTING REDUCED FEED INTAKE IN ANIMALS AND TREATMENT OF DISEASE CONDITIONS

(75) Inventors: James Baber Rowe, Armidale (AU); Christopher William Rowe, Armidale (AU)

(73) Assignee: Precision Nutrition Pty Ltd, Armidale (AU)

( * ) Notice: Subject to any disclaimer, the term of this patent is extended or adjusted under 35 U.S.C. 154(b) by 577 days.

(21) Appl. No.: 12/097,089

(22) PCT Filed: Dec. 15, 2006

(86) PCT No.: PCT/AU2006/001901
§ 371 (c)(1),
(2), (4) Date: Sep. 19, 2008

(87) PCT Pub. No.: WO2007/068055
PCT Pub. Date: Jun. 21, 2007

(65) Prior Publication Data
US 2009/0053188 A1  Feb. 26, 2009

(30) Foreign Application Priority Data
Dec. 15, 2005  (AU) ............................... 2005907069

(51) Int. Cl.
*A61K 38/54* (2006.01)
(52) U.S. Cl. .................. 424/94.2; 514/293; 514/305
(58) Field of Classification Search .................. None
See application file for complete search history.

(56) References Cited

U.S. PATENT DOCUMENTS

| 5,204,361 | A  | 4/1993  | Rowe |
| 5,290,767 | A  | 3/1994  | Rowe |
| 6,303,572 | B1 | 10/2001 | Rowe |
| 6,468,964 | B1 | 10/2002 | Rowe |

FOREIGN PATENT DOCUMENTS

| EP | 0335704 A2    | 10/1989 |
| WO | W09620709 A1  | 7/1996  |
| WO | W09920305 A1  | 4/1999  |
| WO | W02006100263 A2 | 9/2006 |

OTHER PUBLICATIONS

Coe et al., J Anim Sci, 1999, vol. 77, p. 2259-2268.*
Thorniley et al., Australian Journal of Agricultural Research, 1996, 47 (4), p. 539-544.*
Jansen, B. C., The Prevention of Enterotoxaemia (Pulpy Kidney Disease) by Vaccination, Bull. Off. int. Epiz., 67 (11-12), 1967, 1539-1567.
Milne, Elspeth, Grass sickness: an update, In Practice, 19 (3), Mar. 1997, 128-133.
Sterne, M., Clostridial Infections, Vlaams Diergeneeskundig Tijdschrift, Jg. 52, Nr. 6, 1983, 414-425.
Hedderson, E. J., et al., Prospects for vaccination against equine grass sickness, Equine vet. J., 36 (2), 2004, 186-191.
Owens, F. N., et al., Acidosis in Cattle: A Review, J. Anim. Sci., 1998, 76:275-286.
Johnson, K. G., et al., Behavioural changes in stabled horses given nontherapeutic levels of virginiamycin, Equine vet. J., 30 (2), 1998, 139-143.
Slater, M., et al., Descriptive epidemiological study of equine laminitis, Equine vet. J., 27 (5), 1995, 364-367.
Baverud, V., et al., "Antimicrobial Susceptibility of Equine and Environmental Isolates of Clostridium Difficile"; Microbial Drug Resistance, 2004, 10(1):57-63.
Bohnel, H., et al., "Two Cases of Equine Grass Sickness with Evidence for Soil-Borne Origin Involving Botulinum Neurotoxin"; J Vet Med B, 2003, 50:178-182.
Collier, J. et al., "Grass Sickness—the Same Old Suspects but still no Convictions!" Equine Vet J, 2001, 33:540-542.
Cottrell, D.F., et al., "The Neurology and Enterology of Equine Grass Sickness: a Review of Basic Mechanisms"; Neurogastroenterol. Mot., 1999, 11:79-92.
Ding, Z. et al., "No Lactic Acid Absorbed from the Caecum and Rumen of Sheep"; Aust J Agric Res, 1998, 49:293-301.
Doxey, D.L., et al., "A Comparative Study of Normal Equine Populations and Those with Grass Sickness (Dysautonomia) in Eastern Scotland", Equine Vet J, 1991, 23:365-369.
Fintl, C., et al., "Evaluation of Urinalysis as an Aid in the Diagnosis of Equine Grass Sickness", Vet Rec, 2002, 151: 721-724.
Garner, H.E., et al., "Lactic Acidosis: A Factor Associated with Equine Laminitis", Journal of Animal Science, 1977, 45:1037-1041.
George, B.A., et al., "Virginiamycin Effects on Controlling Necrotic Enteritis Infection in Chickens"; Poultry Science, 1982, 61(3):447-450.
Gilmour, J.S., et al., "Some Aspects of the Epidemiology of Equine Grass Sickness", Vet Rec, 1974, 95:77-81.
Godfrey, S.I. et al., "Changes within the Digestive Tract of Sheep Following Engorgement with Barley", Aust. J. Agric. Res., 1992, 44:1093-1101.
Hatheway, C.L., "Toxigenic Clostridia", Clinical Microbiol. Rev., 1990, 3:66-98.
Hunter, L.C., et al., "The Association of *Clostridium botulinum* Type C with Equine Grass Sickness: a Toxicoinfection?" Equine Vet J, 1999, 31:492-499.
Krueger, A.S., et al., "Ultrastructural Study of the Equine Cecum During Onset of Laminitis", Am. J. Vet. Res., 1986, 47:1804-1812.
Langworth, B.F., "*Fusobacterium necrophorum*: Its Characteristics and Role as an Animal Pathogen", Bacteriological Reviews, 1977, 41:373-390.

(Continued)

*Primary Examiner* — Kade Ariani
(74) *Attorney, Agent, or Firm* — Quarles & Brady, LLP

(57) ABSTRACT

The present invention relates to a method for substantially preventing a reduction in feed intake in an animal which occurs when said animal is administered an antibiotic, the method comprising administering to an animal in need of prevention of a reduction in feed intake, increasing doses of a composition comprising one or more antibiotics. The present invention also relates to a method for treating laminitis and fermentative acidosis in an animal in need of said treatment, the method comprising administering increasing doses of a composition comprising one or more antibiotics. The present invention further relates to a method for treating equine grass sickness and pulpy kidney in an animal in need of said treatment, the method comprising administering increasing doses of a composition comprising one or more antibiotics.

4 Claims, 6 Drawing Sheets

OTHER PUBLICATIONS

Lee, G.J., et al., "Changes in Rumen Fluid Composition and in the Rumen Epithelium When Wheat is Introduced to the Diet of Sheep: The Influence of Wheat and Hay Consumption", Aust. J. Agric. Res., 1982, 33:321-333.

Lund, B.M. et al. "Inhibition of Type A and Type B (Proteolytic) *Clostridium botulinum* by Sorbic Acid", Appl Environ Microbiol, 1987, 53:935-941.

McCarthy, H.E, et al., "Epidemiology of Equine Grass Sickness: a Literature Review (1909-1999)", Vet Rec, 2001, 149:293-300.

McGorum, B.C. et al., "Clinicopathological Features Consistent with Both Botulism and Grass Sickness in a Foal", Vet Rec, 2003, 152:334-336.

Murray, A., et al., "Light Microscopy of the Enteric Nervous System of Horses with or without Equine Dysautonomia (Grass Sickness): its Correlation with the Motor Effects of Physostigmine", Vet Res Communications, 1997, 21:507-520.

Nagaraja, T.G., et al., "Liver Abscesses in Feedlot Cattle: a Review", J. Anim. Sci., 1998, 76:287-298.

Newton, J.R., et al., "An Epidemiological Study of Risk Factors Associated with the Recurrence of Equine Grass Sickness (Dysautonomia) on Previously Affected Premises", Equine Vet J, 2004, 36:105-112.

Patra, R.C. et al., "Biochemical Profile of Rumen Liquor, Blood and Urine in Experimental Acidosis in Sheep", Small Ruminant Research, 1996, 19:177-180.

Rowe, J.B., "How Much Acid in the Gut is too Much?", Recent Advances in Animal Nutrition in Australia, 1999, 12:81-89.

Rowe, J.B. et al., "Faecal and Urine Acidity in a Commercial Piggery", Recent Advances in Animal Nutrition in Australia, 1999, 12:15A.

Rowe, J.B. et al., "Prevention of Acidosis and Laminitis Associated with Grain Feeding in Horses", Journal of Nutrition, 1994, 124:2742S-2744S.

Rowe, J.B. et al., "Controlling Acidosis in the Equine Hindgut", Recent Advances in Animal Nutrition in Australia, 1995, pp. 136-142.

Simpson, L.L., "Identification of the Major Steps in Botulinum Toxin Action", Annu Rev Pharmacol Toxicol, 2004, 44:167-193.

Sugiyama, H., et al., "Intraintestinal Toxin in Infant Mice Challenged Intragastrically with *Clostridium botulinum* Spores", Infection and Immunity, 1978, 21:59-63.

Watts, K.A., "Forage and Pasture Management for Laminitic Horses"; Clinical Techniques in Equine Practice, 2004, 3:88-95.

Wood, J.L.N., et al., "A Case-Control Study of Grass Sickness (Equine Dysautonomia) in the United Kingdom", Vet J, 1998, 156:7-14.

* cited by examiner

Increased intake of fermentable carbohydrate    Ingestion of C. botulinum spores Founderguard (virginiamycin)

Fermentative acidosis    Establishment of C. botulinum

Absorption of toxin

Equine grass sickness

METHOD OF PREVENTING REDUCED FEED INTAKE IN ANIMALS AND TREATMENT OF DISEASE CONDITIONS

CROSS REFERENCE TO RELATED APPLICATIONS

This application represents the national stage application of International Application PCT/AU2006/001901 filed Dec. 15, 2006, which claims the benefit of Australian Patent Application 2005907069, filed Dec. 15, 2005, which is incorporated herein by reference in its entirety for all purposes.

TECHNICAL FIELD

The present invention relates to a method for substantially preventing a reduction in feed intake in animals, wherein the reduction results from the introduction of antibiotics into the diet. The invention also relates to the treatment and/or prevention of disorders with antibiotics, such that a reduction in feed intake associated with the introduction of the antibiotic is substantially prevented. The invention further relates to methods for treating equine grass sickness and pulpy kidney.

BACKGROUND ART

Antibiotics such as virginiamycin are used in the treatment of fermentative acidosis and side effects thereof in sheep, cattle and horses and in the management of necrotic enteritis in poultry. There are however problems associated with their use, such as a reduction in feed intake or loss of appetite upon introduction of the antibiotic into the diet. Reduced feed intake leads to loss of weight and less efficient feed conversion in production animals, and can affect athletic performance in performance horses. A sudden decrease in feed intake and reduced rate of digesta flow can lead to mild constipation and create conditions suitable for bacterial proliferation in the digestive tract.

It is known that when virginiamycin is first included in the diets of sheep, cattle and horses feed intake reduces to levels significantly below pre-treatment control levels for between 2 to 4 days before returning to normal. The use of very high concentrations of virginiamycin (500 mg/kg complete feed) has been shown to reduce feed intake in horses before returning to normal. The reason for this reduced feed intake is not known and it is apparent that it is not simply a question of taste and therefore a problem that can be overcome through modifying feed formulation.

Currently there is no known method for overcoming the reduction in feed intake in animals resulting from introduction of antibiotics into the diet. There is therefore a need for a method of preventing a reduction in feed intake in animals, wherein the reduction results from the introduction of antibiotics into the diet. There is also a need for treatments of diseases and conditions using antibiotics wherein the commencement of the treatment regime does not result in a reduction in feed intake.

The present invention is based on the surprising discovery by the inventors that administering increasing doses of antibiotics over a specified time period substantially prevents a reduction in feed intake.

SUMMARY OF THE INVENTION

According to a first aspect of the present invention there is provided a method for substantially preventing a reduction in feed intake in an animal which occurs when said animal is administered an antibiotic, said method comprising administering to said animal in need of prevention of a reduction in feed intake, increasing doses of a composition comprising one or more antibiotics over a specified time period.

According to a second aspect of the present invention there is provided a method for treating laminitis in an animal in need of said treatment, said method comprising administering to said animal, increasing doses of a composition comprising one or more antibiotics over a specified time period.

According to a third aspect of the present invention there is provided a method for treating fermentative acidosis in an animal in need of said treatment, said method comprising administering to said animal, increasing doses of a composition comprising one or more antibiotics over a specified time period.

According to a fourth aspect of the present invention there is provided a method for treating equine grass sickness in an equine animal in need of said treatment, said method comprising administering to said equine animal, increasing doses of a composition comprising one or more antibiotics over a specified time period.

According to a fifth aspect of the present invention there is provided a method for treating pulpy kidney in an animal in need of said treatment, said method comprising administering to said animal, increasing doses of a composition comprising one or more antibiotics over a specified time period.

The following applies to the first through fifth aspects.

The administering of increasing doses of a composition as defined in the second through fifth aspects of the invention also substantially prevents a reduction in feed intake in addition to treating or preventing the condition.

In the method of the first to third aspects, the animal may be an equine animal or a ruminant animal.

In the method of the fifth aspect the animal may be a ruminant animal.

The equine animal may be selected from the group consisting of: a horse, a mule or a donkey.

The ruminant animal may be selected from the group consisting of: cattle, goats, sheep, and deer.

According to a sixth aspect of the present invention there is provided a method for the treatment or prevention of equine grass sickness in an equine animal in need of said treatment or prevention, wherein said method comprises administering an effective amount of an active agent selected from the group consisting of: antibiotics, enzyme preparations, prebiotics and probiotics, and wherein said active agent treats or prevents fermentative acidosis and *Clostridium* spp. infection.

The *Clostridium* spp. infection may be a *Clostridium botulinium* infection.

The *Clostridium botulinium* infection may be a *Clostridium botulinum* type C infection.

The equine animal may be selected from the group consisting of: a horse, a mule or a donkey.

According to a seventh aspect of the present invention there is provided a method for the treatment or prevention of pulpy kidney in an animal in need of said treatment or prevention, wherein said method comprises administering an effective amount of an active agent selected from the group consisting of: antibiotics, enzyme preparations, prebiotics and probiotics, and wherein said active agent treats or prevents fermentative acidosis and *Clostridium* spp. infection.

The *Clostridium* spp. infection may be a *Clostridium perfringens* infection.

The *Clostridium perfringens* infection may be a *Clostridium perfringens* Type D infection.

The animal may be a ruminant animal selected from the group consisting of: cattle, goats, sheep, and deer.

According to an eighth aspect of the present invention there is provided a method for the treatment or prevention of equine grass sickness in an equine animal in need of said treatment or prevention, wherein said method comprises administering an effective amount of an enzyme preparation, wherein said enzyme preparation treats or prevents fermentative acidosis and increases the rate of digesta flow, thereby inhibiting proliferation of *Clostridium* spp. infection.

The *Clostridium* spp. infection may be a *Clostridium botulinium* infection. The *Clostridium botulinium* infection may be a *Clostridium botulinium* type C infection.

The equine animal may be selected from the group consisting of: a horse, a mule or a donkey.

According to a ninth aspect of the present invention there is provided a method for the treatment or prevention of pulpy kidney in an animal in need of said treatment or prevention, wherein said method comprises administering an effective amount of an enzyme preparation, wherein said enzyme preparation treats or prevents fermentative acidosis and increases the rate of digesta flow, thereby inhibiting proliferation of *Clostridium* spp, infection.

The *Clostridium* spp. infection may be a *Clostridium perfringens* infection.

The *Clostridium perfringens* infection may be a *Clostridium perfringens* type D infection.

The animal may be a ruminant animal selected from the group consisting of: cattle, goats, sheep, and deer.

According to an tenth aspect of the present invention there is provided a method for the treatment or prevention of equine grass sickness in an equine animal in need of said treatment or prevention, wherein said method comprises vaccination of said animal against *Clostridium* spp. infection, together with vaccination against lactic acid producing bacteria.

The lactic acid producing bacteria may be selected from the group consisting of: *Streptococcus bovis, S. equinus* and *Selenomonas ruminantium*.

The *Clostridium* spp. infection may be a *Clostridium botulinium* infection.

The *Clostridium* botulinium infection may be a *Clostridium botulinum* type C infection.

The equine animal may be selected from the group consisting of: a horse, a mule or a donkey.

According to a eleventh aspect of the present invention there is provided a method for the treatment or prevention of pulpy kidney in an animal in need of said treatment or prevention, wherein said method comprises vaccination of said animal against *Clostridium* spp. infection, together with vaccination against lactic acid producing bacteria.

The lactic acid producing bacteria may be selected from the group consisting of: *Streptococcus bovis, S. equinus* and *Selenomonas ruminantium*.

The *Clostridium* spp. infection may be a *Clostridium perfringens* infection.

The *Clostridium perfringens* infection may be a *Clostridium perfringens* type D infection.

The animal may be a ruminant animal selected from the group consisting of: cattle, goats, sheep, and deer.

DEFINITIONS

In the context of this specification, the term "comprising" means "including principally, but not necessarily solely". Furthermore, variations of the word "comprising", such as "comprise" and "comprises", have correspondingly varied meanings.

As used herein the terms "treatment", "treating" and variations thereof, refer to any and all uses which remedy a disease state or symptoms, prevent the establishment of disease, or otherwise prevent, hinder, retard, or reverse the progression of disease or other undesirable symptoms in any way whatsoever.

As used herein the term "effective amount" includes within its meaning a non-toxic but sufficient amount of an agent or compound to provide the desired therapeutic or prophylactic effect. The exact amount required will vary from animal to animal depending on factors such as the species being treated, the age and general condition of the animal, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the term "fermentative acidosis" or "acidosis" includes within its meaning increased acid concentration in the gastrointestinal tract resulting from fermentation of carbohydrate that reduces the pH from normal levels by at least 1 pH unit (for example reducing the pH of colonic digesta from >6.5 to <5.5).

BRIEF DESCRIPTION OF THE DRAWINGS

The present invention will now be described with reference to the accompanying drawings.

FIG. 4 shows a summary of the multiple effects of virginiamycin through: direct antibiotic effect on the pathogen (*C. botulinum*); the reduction in acid accumulation to reduce the impact of this factor as a predisposing factor or trigger for *C. botulinum* establishment, toxin production or toxin absorption; and by synergistic action achieved through the simultaneous inhibition of *C. botulinum* and acidosis to reduce the risk of equine grass sickness.

DETAILED DESCRIPTION OF THE INVENTION

Figure 1:
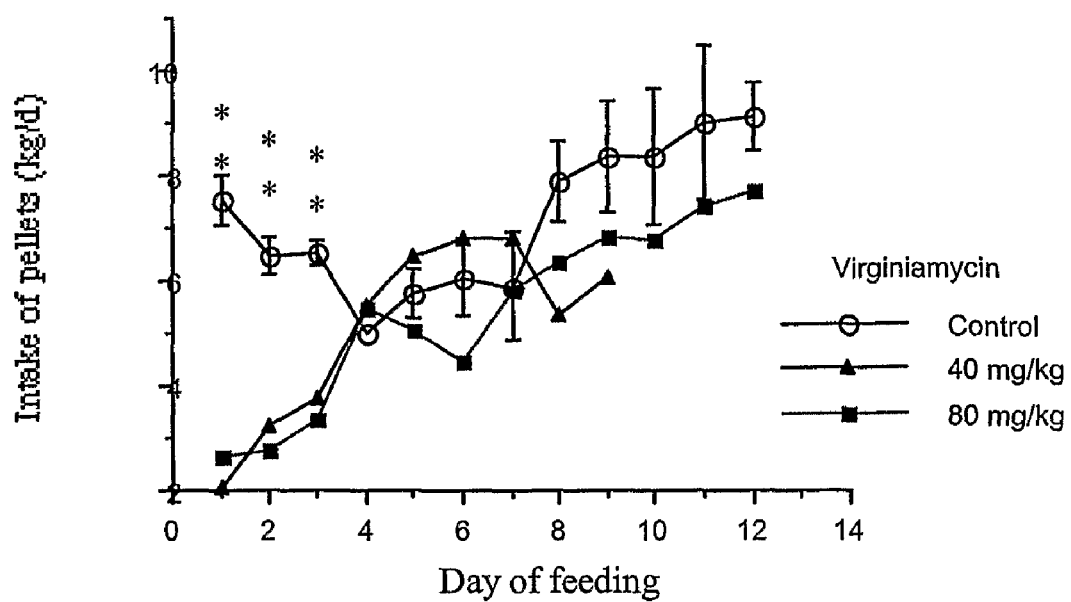
FIG. 1 shows intake by horses of a pelleted portion of the diet containing no medication, or virginiamycin at concentrations of 40 or 80 mg/kg. ** Significant (p<0.05) treatment effect. The fall dose of virginiamycin was administered from day 1.

Methods for Substantially Preventing a Reduction in Feed Intake and Use of the Method for Treatment of Disease Conditions The methods of the first to fifth aspects of the invention involve gradually increasing the concentration or dose of the antibiotic over several days until the appropriate full dose rate is achieved. Such a method allows effective treatment of disease conditions such as laminitis, fermentative acidosis, equine grass sickness and pulpy kidney.

The antibiotic may be selected from the group consisting of: a glycopeptide antibiotic, a glycolipid antibiotic, a staphlomycin antibiotic, a polypeptide antibiotic, a macrolide antibiotic, a streptogramin antibiotic, a pristinamycin antibiotic, a sulfur-containing peptide antibiotic, a lincosamide antibiotic, a glycolipodipepsipeptide antibiotic, a fluoroquinalone antibiotic, a tiamulin or a nitrofuran antibiotic, a tetracycline antibiotic, a penicillin antibiotic, a polythiazole antibiotic, an ionophore antibiotic (for ruminants only), or any other antibiotic which is active against gram positive bacteria, or any combination thereof.

More specifically, the antibiotic may be selected from the group consisting of: avoparcin, vancomycin, flavomycin (bambermycin), virginiamycin, virginiamycin A, virginiamycin M, bacitracin zinc, bacitracin, methylene disalicyclate, polymixins (B and E), tylosin, spiramycin, josamycin, spectinomycin, erythromycin, thiopeptone, sulfomycin, thiostrepton, sporangiomycin, siomycin, taitoinycin, lincomycin, clindamycin, tiamulin, nitrofurantoin, nitrofurazone, furazolidone, chlortetracycline, oxytetracycline, nosiheptide, novobiocin sodium, bottromycin tartrate, streptogramin, nitrovin (payzone), enramycin, penicillin V, lasalccid, tetronasin, naracin, salinomycin, ampicillin, vancomycin, penicillin-G, ramoplannin, teicoplanin, metronidazole, gentamycin cephalosporin, lincosamide.

The antibiotics may be used in combination with any antibiotics active against lactic acid producing bacteria such as *Streptococcus* spp. *Clostridium* spp. and *Lactobacillus* spp.

The specified time period may be between: 1 and 10 days, 1 and 9 days, 1 and 8 days, 1 and 7 days, 1 and 6 days 1 and 5 days, 1 and 4 days 1 and 3 days, 1 and 2 days. The specified time period may be 1, 2, 3, 4, 5, 6, 7, 8, 9 or 10 days.

The increasing doses of the composition may be administered at an increasing proportion from between 5% to 100% of a full dose.

The increasing doses of the composition may comprise a first dose which is between 10% and 35% of a full dose, and a second dose which is between 40% and 60% of a full dose.

The increasing doses of the composition may comprise a first dose which is between 10% and 35% of a full dose, a second dose which is between 40% and 60% of a full dose, and a third dose which is between 65% and 85% of a full dose.

The increasing doses of the composition may comprise a first dose which is between 10% and 25% of a full dose, a second dose which is between 30% and 50% of a full dose, a third dose which is 55% and 75% of a full dose and a fourth dose which is between 80% to 100% of the full dose.

In one embodiment, the first dose is about 33% of a full dose, the second dose is about 66% of a full dose and the third dose is 100% of a full dose.

In another embodiment, the first dose is about 25% of the full dose, the second dose is about 50% of a full dose, the third dose is about 75% of a full dose and the fourth dose is 100% of a full dose.

In yet another embodiment, the first dose is about 20% of a full dose, the second dose is about 40% of a full dose, the third dose is about 60% of a full dose, the fourth dose is about 80% of a full dose and the fifth dose is 100% of a full dose.

The increasing doses may be given on a daily basis, or alternatively multiple increasing doses may be given in a single day, or alternatively the increasing doses may be given once every two days.

The full dose may be between: 0.001 and 5 mg/kg bodyweight per day, 0.005 and 5 mg/kg bodyweight per day, 0.01 and 5 mg/kg bodyweight per day, 0.05 and 5 mg/kg bodyweight per day, 0.075 and 5 mg/kg bodyweight per day, 0.1 and 5 mg/kg bodyweight per day, 0.25 and 5 mg/kg bodyweight per day, 0.5 to 5 mg/kg bodyweight per day, between 1 and 5 mg/kg bodyweight per day, 1.25 and 5 mg/kg bodyweight per day, 1.5 and 5 mg/kg bodyweight per day, between 1.75 and 5 mg/kg bodyweight per day, 2 and 5 mg/kg bodyweight per day, 2.25 and 5 mg/kg bodyweight per day, 2.5 and 5 mg/kg bodyweight per day, 2.75 and 5 mg/kg bodyweight per day, 3 and 5 mg/kg bodyweight per day, 3 and 5 mg/kg bodyweight per day, 3.25 and 5 mg/kg bodyweight per day, 3.5 and 5 mg/kg bodyweight per day, 3.75 mg/kg bodyweight per day, 4 and 5 mg/kg bodyweight per day, 0.001 to 4.75 mg/kg bodyweight per day, 0.001 to 4.5 mg/kg bodyweight per day, 0.001 to 4.5 mg/kg bodyweight per day, 0.001 to 4.25 mg/kg bodyweight per day, 0.001 to 4 mg/kg bodyweight per day, 0.001 to 3.75 mg/kg bodyweight per day, 0.001 to 3.5 mg/kg bodyweight per day, 0.001 to 3.25 mg/kg bodyweight per day, 0.001 to 3 mg/kg bodyweight per day, 0.001 to 2.75 mg/kg bodyweight per day, 0.001 to 2.5 mg/kg bodyweight per day, 0.001 to 2.25 mg/kg bodyweight per day, 0.001 to 2 mg/kg bodyweight per day, 0.001 to 1.75 mg/kg bodyweight per day, 0.001 to 1.5 mg/kg bodyweight per day, 0.001 to 1.25 mg/kg bodyweight per day, 0.001 to 1 mg/kg bodyweight per day, 0.001 to 0.75 mg/kg bodyweight per day, 0.001 and 0.5 mg/kg bodyweight per day, 0.01 and 2, mg/kg bodyweight per day, 0.05 and 1 mg/kg bodyweight per day, 0.1 and 1 mg/kg bodyweight per day, between 1 and 3 mg/kg bodyweight per day, between 1.4 and 2.6 mg/kg bodyweight per day.

The full dose may be selected from the group consisting of: 0.5 mg/kg bodyweight per day, 1.4 mg/kg bodyweight per day and 2.6 mg/kg bodyweight per day.

In an embodiment of the first aspect, the time period may be 3 days, the full dose may be 0.5 mg/kg bodyweight per day, and the increasing doses of the composition may be 33% of the full dose on day 1, 66% of the full dose on day 2, and 100% of the full dose on day 3.

In an embodiment of the first aspect, the time period may be 4 days, the full dose may be 0.5 mg/kg bodyweight per day, and the increasing doses of the composition may be 25% of the full dose on day 1, 50% of the full dose on day 2, 75% of the full dose on day 3 and 100% of the full dose on day 4.

In an embodiment of the first aspect, the time period may be 5 days, the full dose may be 0.5 mg/kg bodyweight per day, and the increasing doses of the composition may be 20% of the full dose on day 1, 40% of the full dose on day 2, 60% of the full dose on day 3, 80% of the full dose on day 4 and 100% of the full dose on day 5.

With gradually increasing doses of virginiamycin for example, there is no detectable decrease in feed intake compared to pre-medication levels. This compares with a significant decrease in intake associated with sudden introduction of the full dose rate to an average of around 80% of the pretreatment level of feed intake and persisting for between 2 and 5 days from the start of treatment.

The time period over which the dose rate is increased and the incremental increase in dose rate may be determined by the full dose rate, the feeding regime and the importance of constant feed intake in terms of the production or performance criteria for the animals being treated. By increasing the dose rate gradually over 3 to 7 days the reduction in feed intake normally associated with introduction of an antibiotic into the diet can be largely overcome. As a result of this finding, conditions which are currently treated with antibiotics, such as laminitis and fermentative acidosis may be treated without the associated reduction in feed intake that occurs under present treatment regimes and without any confounding effects of reduced rates of digesta flow.

When being prepared for a significant change in the amount or nature of readily fermentable carbohydrate in the diet, or for a possible bacterial challenge, a high full dose of the antibiotic may be required to provide the appropriate level of protection. Under these conditions gradual increases in the dose of the antibiotic should take place over 3 or 7 days. On the other hand, where average or low dose rates are required, the dose build up can take place over 3 to 4 days.

For example, a horse known to consume higher than average amounts of feed and gain weight faster than average would, before moving to a paddock with more than 3 tonnes dry matter/ha of very lush green feed, in an area known to have a history of equine grass sickness, require a higher level of virginiamycin (say about 2 mg/kg body weight) and a gradual introduction over about 6 days to reach the full dose rate before moving into the new paddock. On the other hand a horse known to consume below average amounts of feed before being moved to paddock with 2 tonnes dry matter/ha of moderately lush pasture in a region not known to have a history of equine grass sickness, may only require about 0.75 mg/kg body weight and gradual introduction over about 4 days to reach full dose rate.

In another example, where a horse is being moved from an area without any history of equine grass sickness to a property where horses are known to have died from equine grass sickness, particularly if the move takes place during spring or autumn, the horse should be treated with virginiamycin at increasing dose rates such as 0.2 mg/kg body weight on day 1, 0.4 mg/kg on day 2, 0.8 mg/kg on day 3, 1.2 mg/kg on day 4 and subsequent days. The horse can be moved on or after day 5 and daily dosing continued for as long the period of high risk is considered to apply. The same treatment regime should be applied to horses prior to moving them to a new paddock with abundant quantities of fresh spring or autumn pasture.

A further factor that needs to be considered in determining dose rate and the introductory regime is the timing of the dietary change or bacterial challenge. Experiments in horses (see Example 3 below) show that low dose rates such as 0.1 mg virginiamycin per kg bodyweight per day may not be effective in preventing over production of lactic acid, and therefore may not be effective in preventing fermentative acidosis. As such, the full dose should be determined according to the particular animal, any dietary change, and/or any bacterial challenge that may present.

Dose rates in the range of 0.4 to 0.7 mg virginiamycin per kg bodyweight per day have been found to result in partial and variable levels of controlling lactic acid production after three to four days, while dose rates over 1.4 mg virginiamycin per kg body weight produce almost complete control after two days of treatment. Therefore, horses that are introduced gradually to virginiamycin should be treated with at least 0.75 mg virginiamycin per kg body weight for at least two days before being exposed to diets or bacterial challenges that may be harmful.

Prior to the discovery on which the present invention is based, it was not known how to administer antibiotics such as virginiamycin to ruminants and horses without the unwanted consequence of a transitory reduction in feed intake. The sudden introduction of virginiamycin to sheep, cattle or horses at dose rates of 0.5 mg virginiamycin per kg body weight and above, or concentrations of virginiamycin of 20 g/tonne and above, reduce feed intake by 20% or more and can adversely affect production, performance and/or digestive function.

Administration of virginiamycin at dose rates and/or concentrations below those that result in decreased feed intake for at least three days before administration of virginiamycin at concentrations and dose rates known to reduce feed intake, will result in animals maintaining feed intake at pre-treatment levels.

Based on the teaching herein, those skilled in the art would, without undue trial and experimentation, be able to determine the appropriate increase in the antibiotic dose rate that is required depending on the prevailing conditions (e.g. the type of animal to be treated, a dietary change, the amount of antibiotic known to cause a decrease in feed intake etc.) in order to substantially prevent a reduction in feed intake, and also to treat disease conditions such as fermentative acidosis, laminitis, equine grass sickness and pulpy kidney.

There is currently no known method of using antibiotic compounds for treatment or prevention of equine grass sickness or pulpy kidney. The fourth and fifth aspects of the invention are based on the discovery by the inventors that a particularly effective method for controlling equine grass sickness and pulpy kidney is achievable through the use of gradually increasing doses of antibiotic as per the method of the first aspect of the invention.

Equine grass sickness and pulpy kidney are multi-factor disease conditions mediated by *Clostridium* spp. pathogens under dietary conditions likely to produce fermentative acidosis in the rumen, caecum and/or colon. Acidosis reduces gut motility and can cause stasis which is considered to be a possible factor facilitating proliferation and colonisation of the intestine by *Clostridium* spp. Acidosis is also known to cause significant damage to the ruminal epithelium (ruminitis) and to the large intestine wall, and this damage is likely to facilitate or increase the rate of absorption of clostridial toxins from the gut. Damage to the gut integrity is well illustrated by the absorption of bacteria from the gut during acidosis and the development of liver abscesses in feedlot cattle.

Figure 5:
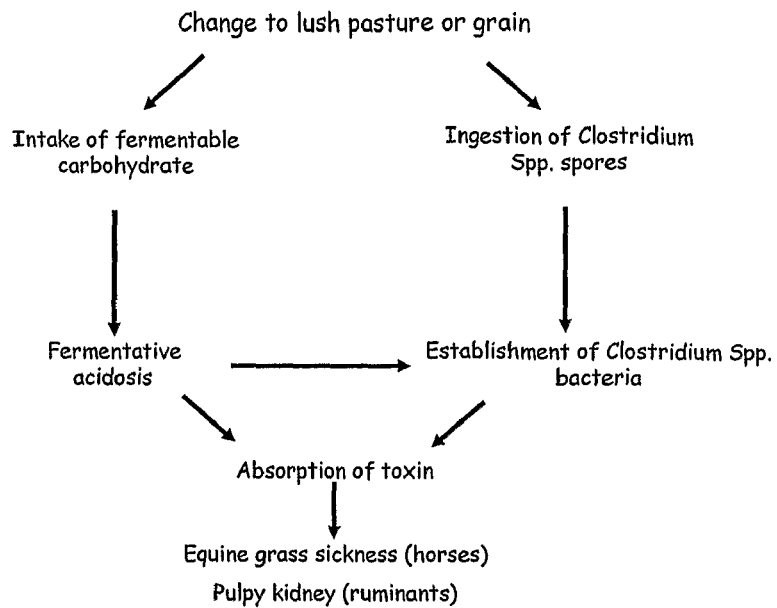
FIG. 5 shows (a) the aetiology of the development of equine grass sickness and pulpy kidney illustrating the requirement for acidosis to predispose the gastrointestinal tract to colonization with *Clostridium* spp. and allow absorption of toxin and (b) the role of virginiamycin in reducing the risk of acidosis and also having a direct antibiotic effect on *Clostridium* spp., thereby acting synergistically to reduce the risk of equine grass sickness in horses and pulpy kidney in ruminants.
Figure 5:
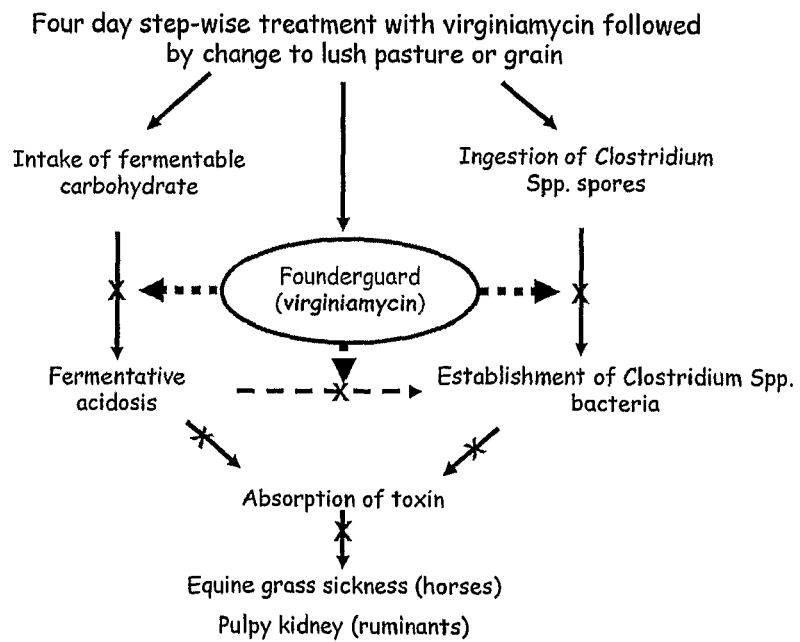
Figure 6:
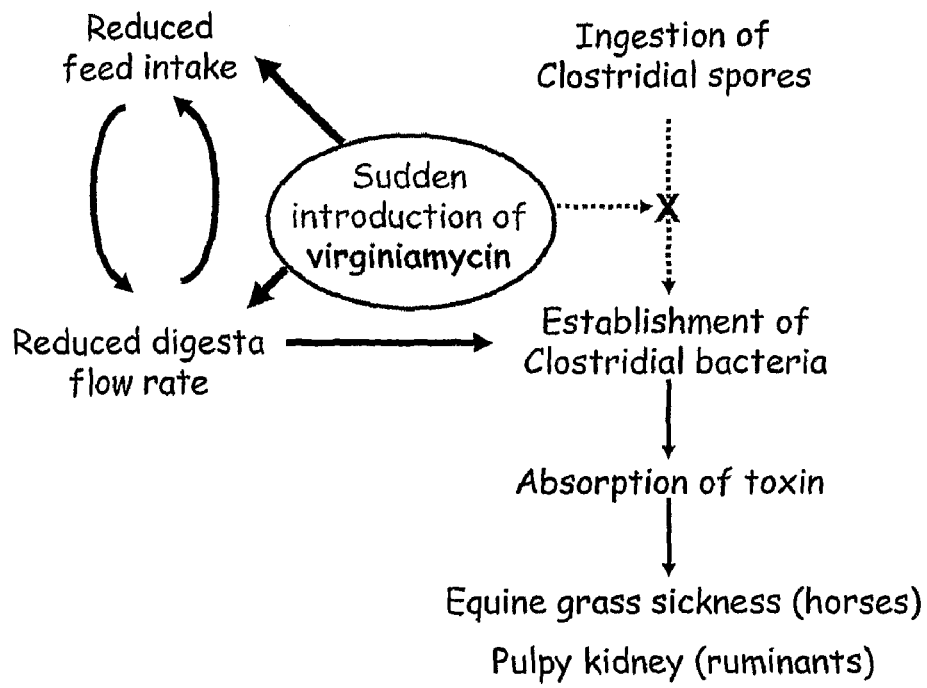
FIG. 6 shows (a) the effect of introducing a full dose of virginiamycin from day 1 on reduced feed intake, reduced digesta flow and the negative feedback of these two effects to produce conditions that are potentially favourable for colonisation of Clostridial bacteria and could potentially increase the risk of equine grass sickness or pulpy kidney despite the antibiotic effect of virginiamycin on *Clostridium* spp. and (b) the benefits of gradual introduction of virginiamycin resulting in no reduction in feed intake and no decrease in the rate of digesta flow while retaining its antibiotic activity.
Figure 6:
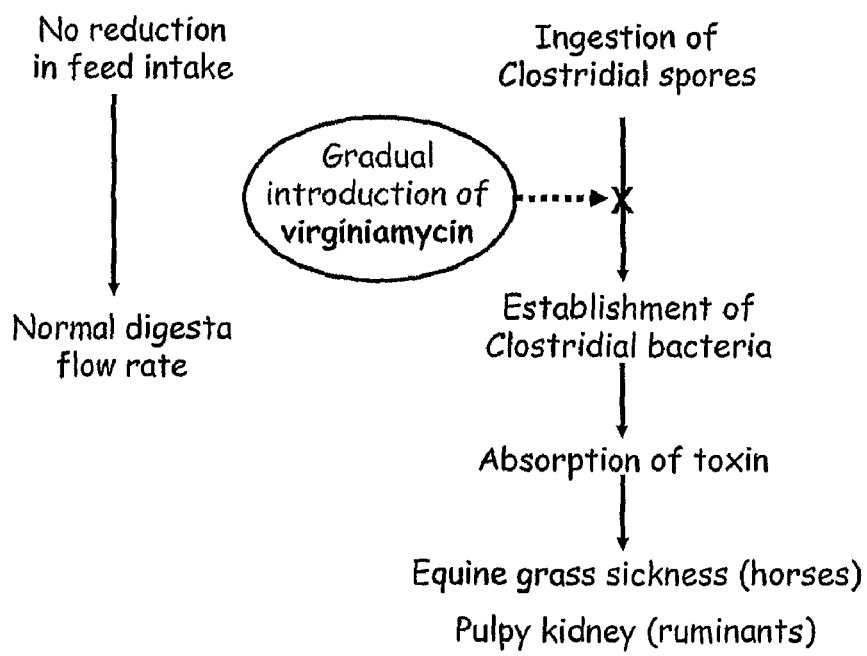

Slower digesta flow may also contribute to the development of equine grass sickness and pulpy kidney. Reduced digesta flow has a similar effect to that of fermentative acidosis in creating conditions suitable for proliferation of *Clostridial* spp. (see FIG. 6a). One cause of slower digesta flow is a sudden introduction of a full dose of antibiotics into the diet. As such, in order to control equine grass sickness and pulpy kidney it is beneficial to maintain the digesta flow rate in addition to controlling fermentative acidosis and the *Clostridial* spp. bacteria. Slow digesta flow that results from a sudden introduction of a full dose of an antibiotic into the diet can be inhibited by administering increasing doses of the antibiotic in accordance with the method described in the first aspect. Reference to FIGS. 5(b) and 6(b) depicts the synergistic effect of the administration of increasing doses of the antibiotic virginiamycin in preventing fermentative acidosis, preventing *Clostridium* spp. infection and maintaining normal digesta flow rate.

Treatment of Equine Grass Sickness and Pulpy Kidney

The present inventors have surprisingly discovered that administration of an effective amount of an active agent capable of treating or preventing fermentative acidosis and *Clostridium* spp. infection provides an effective treatment for equine grass sickness. The present inventors have also surprisingly discovered that administration of an effective amount of an agent capable of treating or preventing fermentative acidosis and *Clostridium* spp. infection provides an effective treatment for pulpy kidney.

The sixth to ninth aspects of the invention may be exemplified by assessing the modulating effects of virginiamycin in the treatment of equine grass sickness and pulpy kidney. However, it will be appreciated that the concept is applicable to other agents capable of treating or preventing fermentative acidosis and *Clostridium* spp. infection.

In one aspect of the invention, control of the condition equine grass sickness is achieved through the discovery that virginiamycin acts via two separate but synergistic pathways both important in the aetiology of the disease. The first pathway is the direct is antibiotic effect of virginiamycin on the putative *Clostridium* spp. pathogen *Clostridium botulinium*, and the second pathway is the effect of virginiamycin in treating fermentative acidosis. The effect of virginiamycin on these two pathways is summarized in FIG. 4 in the context of equine grass sickness.

In another aspect of the invention, control of pulpy kidney is achieved through the discovery that virginiamycin acts via a direct antibiotic effect on the putative *Clostridium* spp. pathogen, *Clostridium perfringens*, and also via the treatment of fermentative acidosis.

In the tenth and eleventh aspects of the invention, vaccination against lactic acid producing bacteria, together with vaccination against *Clostridium* spp. bacteria, for example, *Clostridium perfringens*, can provide more effective control of pulpy kidney than vaccination against *Clostridium* spp. alone. Similarly, simultaneous vaccination against lactic acid producing bacteria and *Clostridium* spp. bacteria, for example *Clostridium botulinuin*, can provide more effective control of equine grass sickness than vaccination against *Clostridium* spp. alone.

Dosage Rates of Active Agents

The effective dose level for any particular animal will depend upon a variety of factors including: the disorder being treated and the severity of risk that the disorder will occur; activity of the agent employed; the composition employed; the age, body weight, general health, sex and diet of the animal; the time of administration; the route of administration; the rate of sequestration of the compound or agent; the duration of the treatment; drugs used in combination or coincidental with the treatment, together with other related factors well known in medicine.

Generally, the active agent is administered regularly throughout the period the animal is subjected to a high carbohydrate diet or to sugars or other fermentable compounds which are rapidly fermented in the rumen and/or not efficiently absorbed prior or reaching the large intestine, colon and caecum.

The active agent may be administered twice per week, every second day or 1-3 times daily. Alternatively, the active agent is administered once daily or can be included in feeds. They can be fed as powders or suspended in water, included in pellets as well as being fed in premixes. Usually, the treatment will consist of administering one dose daily of the active agent for a period sufficient to control the accumulation of acid by fermentation of the carbohydrate in the gastrointestinal tract and also to control *Clostridium* spp. infection. Dosing may continue while sources of carbohydrate known to cause problems of equine grass sickness or pulpy kidney in the gastrointestinal tract are included in the diet.

The active agent may be administered in a single dose immediately before consuming meals containing sources of carbohydrate which are poorly digested and rapidly fermented. Alternatively, the active agent is administered for one day prior to and daily during the consumption of excessive quantities of food stuffs containing readily fermentable carbohydrates.

Dosages of the agent will typically range from between any one of the following: 0.01 and 100 mg per kg of bodyweight; 0.01 and 75 mg per kg of bodyweight; 0.01 and 50 mg per kg of bodyweight; 0.01 and 25 mg per kg of bodyweight; 0.01 and 15 mg per kg of bodyweight; 0.01 and 10 mg per kg of bodyweight; and 0.01 and 5 mg per kg of bodyweight. More typically dosages will range from between 0.02 and 2.0 mg per kg of bodyweight. More typically dosages will range from between 0.05 and 1.0 mg per kg of bodyweight. Even more typically dosages will range from between 0.1 and 0.5 mg per kg of bodyweight. Yet even more typically, the dosage rate will be 0.5 mg per kg of bodyweight.

Antibiotic

The administered dose of the antibiotic can vary and will depend on several factors, such as the condition, age and size of the animal, as well as the nature of the lactic acid producing bacteria.

The antibiotic is active against gram-positive lactic acid producing microorganisms and *Clostridium* spp. For example, the antibiotic may be selected from the group consisting of: glycopeptide antibiotics, such as, ardacin, avoparcin, teicoplanin, pantomycin, CTA-A1, TD-A3 or vancomycin. In another example, the antibiotic may be selected from the group consisting of: glycolipid antibiotics, such as flavomycin (bambermycin). In yet another example, the antibiotic may be a Streptogramin antibiotic, such as an virginiamycin, or a polypeptide antibiotic, such as bacitracin zinc, bacitracin methylene disalicylate, virginiamycin S or polymixins (B & E). In yet another example, the antibiotic may be a macrolide antibiotic, such as tylosin, spiramycin, virginiamycin M, josamycin, spectinomycin or erythromycin. In yet another example, the antibiotic may be an ionophore antibiotic, such as monensin, salinomycin, M139603 (provided that the ionophore antibiotics are only used in ruminants for pulpy kidney and not in horses, since ionophore antibiotics are toxic to equines). In a further example, the antibiotic may be a sulfur-containing peptide antibiotic, such as thiopeptone, thiopeptin, sulfomycin, thiostrepton, sporangiomycin, siomycin or taitomycin. In yet a further example the antibiotic may be a lincosamide antibiotic, such as lincomycin or clindamycin. In a further example, the antibiotic may be a nitrofuran antibiotic such as, nitrofurantoin, nitrofurazone or furazolidone. In yet another example, the antibiotic may be a tetracycline antibiotic such as chlortetracycline, oxytetracycline, doxycycline or minocycline. In a further example, the antibiotic may be a beta-lactamase or penicillin antibiotic, such as a penicillinase-resistant penicillin, for example oxacillin, methicillin, penicillin V, penicillin-G or ampicillin. In a further example, the antibiotic may be a glycolipidopeptipeptide antibiotic, such as ramoplanin. In a further example, the antibiotic may be a polythiazole antibiotic, such as nosiheptide. In a further example, the antibiotic may be a pleuromutilin such as tiamulin. In a further example, the antibiotic may be an ionophore antibiotic, such as lasalocid, tetronasin, naracin, salinomycin, novobiocin sodium, orbottromycin tartrate. In yet a further example, the antibiotic may be a streptogramin antibiotic, such as quinupristin/dalfopristin (RP 59500; Synercid) or streptogramin combinations [quinupristin/dalfopristin (RP 59500; Synercid)], eveminomycin derivatives (SCH 27899), oxazolidinones (U-100572, U-100766). In a further example, the antibiotic may be a fluoroquinolone antibiotic, such as ciprofloxacin, ofloxacin, clinafloxacin, DU 6859a, sitafloxacin, gatifloxacin, gemifloxacin, grepafloxacin, levofloxacin, sparfloxacin, eprofloxacin or trovafloxacin. In yet a further example, the antibiotic may be a beta-lactam antibiotic. In still a further example, the antibiotic may be nitrovin (payzone), metronidazole (flagyl), enramycin, mupiricin, magainin or chloramphenicols and related compounds, including florphenicol thiamphenicol, and any combination thereof.

The antibiotics may be used in combination with any antibiotic agents active against lactic acid producing bacteria such as *Streptococcus* spp. *Clostridium* spp. *Selenomonas* spp. and *Lactobacillus* spp.

Typically, the antibiotic is administered at a rate of between 1 and 100 mg per kg of dry weight of food. More typically, the antibiotic is administered at a rate of between 1 and 75 mg per kg of dry weight of food. Even more typically, the antibiotic is administered at a rate of between 1 and 50 mg per kg of dry weight of food. Yet even more typically, the antibiotic is administered at a rate of between 5 and 40 mg per kg of dry weight of food.

Typically, antibiotic preparations are selected and/or formulated for delivery to the hind gut and for little or no absorption from the digestive tract. Formulations include encapsulation and/or coating with materials resistant to acid and enzymic digestion in the stomach and small intestine. Formulation can also include chemical treatment to reduce the solubility of the antibiotic.

Where horses are considered to be approaching a situation associated with elevated risk of contracting equine grass sickness, based on known environmental, management and/or nutritional conditions, treatment with the appropriate active agent should commence at least 5 days before horses are exposed to that risk. Examples of predictable high-risk situations include moving a horse from an area without any history of equine grass sickness to a property where horses are known to have died from equine grass sickness, particularly if the move takes place during spring or autumn. Similarly for pulpy kidney in ruminants, treatment with the appropriate active agent should commence at least 5 days before animals are exposed to high-risk dietary conditions, such as an introduction of a grain-based diet or moving on to a lush green pasture.

In terms of treatment with virginiamycin, in order to achieve effective concentrations of virginiamycin to control lactic acid producing bacteria and *Clostridium*. spp. throughout the digestive tract, through to the terminal colon, it is necessary to administer at least two daily doses of virginiamycin equivalent to 1.0 mg per kg body weight per day (or more) before animals are exposed to high levels of fermentable carbohydrate and/or *Clostridium* spp.

Enzyme Preparation

The enzyme preparation is active against lactic acid producing gram-negative bacteria, and is typically designed to reduce the passage of fermentable carbohydrate to the hind gut through improving the digestion and absorption in the intestine of starches, disaccharides, oligosaccharides, non-starch polysaccharides, protein starch complexes and any polysaccharide which is incompletely digested in the intestine, but which is readily fermentable in the hind gut. Enzymes can also prevent a decreased rate of digesta flow by breaking down non-starch polysaccharides that contribute to increased viscosity of digesta.

Examples of preferred enzymes for the break down of non-starch polysaccharides and starches include the following: glyconases including: amylase, maltase, invertase, α-glucosidases, emulsin, and amyloglucosidase; β-glucanases β-glucanase, xylanase; enzymes which break down galactosides of the raffinosse series and other α-galactosides including α-galactosidase, enzymes which break down the proteins forming part of the matrix surrounding starches, sugars and non-starch carbohydrates in plant material, including: pepsin, trypsin, trypsinogen, chymotrypsin and natural and synthetic proteolytic enzymes of chemical or microbial origin, enzymes which depolymerise non-starch polysaccharides including: arabinoxylans and β-glucans, and enzymes active in the break down of cellulose, including: cellulase, enzymes active in the break down of colloidal polysaccharides, pectic substances, which include: galactouronans, galactan and arabinans, as well as the neutral polysaccharides such as xyloglucans and galactomannans and other non-starch polysaccharides such as: rhamnogalactouronan with arabinose and galactose, arabinogalactan, glucan, xyloglucan, galactouronan with arabinose and uronan with arabinose. These enzymes can be used individually or in combination.

The enzyme preparations active against lactic acid accumulation from gram-negative lactic acid producing microorganisms may be used in conjunction with the antibiotic agent.

As above, the administered dose of the enzyme preparation can vary and will depend on several factors, such as the condition, age and size of the human or animal patient, as well as the nature of the carbohydrate. Dosages will typically range from between 0.01 and 50 g/kg food dry matter. Typically, the enzyme is administered at a rate of between 0.1 and 3 g per kg of dry weight of food. More typically, the enzyme is administered at a rate of between 1 g per kg of dry weight of food.

Probiotic

The probiotic preparations include bacteria selected from the group consisting of: *Megasphera, Veillenolla, Selenomonas, Propionibacterium, Anaerovibrio* and *Peptococcus*.

Probiotic agents may be active against lactic acid producing gram-negative bacteria. For example, the probiotic reduces lactic acid accumulation by: formation of alternative end products of fermentation; through increased utilisation of lactic acid; or through the conversion of lactic acid to volatile fatty acids which can be absorbed from the gut, thereby reducing acidity in the gut.

Typically, preferred probiotic preparations include bacteria which ferment starch and sugars to end products other than lactic acid, (ie volatile fatty acids), and bacteria which convert lactic acid to volatile fatty acids. More typically, microorganisms such as *Megasphera elsdeniii* and certain strains of *Selenomonas ruminantium* can ferment sugars or starch without accumulation of lactic acid and these strains can be used to reduce lactic acid accumulation.

More typically, the probiotic preparations may include bacteria that belong to the genera: *Succinomonas, Butyrivibrio, Bacteroides* and *Succinivibrio*. These bacteria can be used individually or in combination. More typically, the probiotic preparations may include anaerobic bacteria. Even more typically, the probiotic preparations may include bacteria selected from the group consisting of: *Megasphera, Veillenolla, Selenomonas, Propionibacterium, Anaerovibrio* and *Peptococcus*. These bacteria can be used individually or in combination. Still more typically, preferred probiotic preparations include yeast and mycelial preparations capable of utilising lactic acid, and converting lactic acid to volatile fatty acids and other end products. Yet still more typically, the probiotic preparations may include yeast and mycelial preparations such as Yea-Sacc.

Typically, the administered dose of the probiotic preparation can vary between $10^4$ and $10^{12}$ bacteria per kg of body weight. More typically, dose of the probiotic preparation can vary between $10^4$ and $10^{10}$ per kg of body weight. Even more typically, dose of the probiotic preparation can vary between $10^4$ and $10^6$ per kg of body weight.

Typically, probiotics are formulated in such a way as to deliver viable bacteria and/or other microorganisms to gastrointestinal tract including the hind gut. These formulation techniques include coatings and encapsulation using materials resistant to gastric and intestinal digestion.

Vaccines

Vaccines to activate the immune system against lactic acid producing bacteria and *Clostridium* spp. may be used to treat or prevent equine grass sickness and pulpy kidney.

The vaccine composition(s) may be synergistic.

Typically vaccine preparations include *Clostridium* spp. bacteria and bacteria responsible for lactic acid production in the rumen, caecum or colon.

More typically the bacteria to be used in vaccine preparations against lactic acid producing bacteria include bacteria that belong to the genera: *Streptococcus bovis, Streptococcus equines, Selenomonas ruminantium*. These bacteria can be used individually or in combination.

The vaccines may comprise live or dead intact cells of *Clostridium* spp. bacteria and bacteria responsible for lactic acid production in the rumen, caecum or colon, together with outer membrane and associated proteins of these bacteria and/or a fragment(s) of these bacteria present as an immunogenic polypeptide glycopeptide or the like.

Vaccination against lactic acid producing bacteria and *Clostridium* spp. bacteria may be performed simultaneously using a single vaccine composition capable of vaccinating against *Clostridium* spp. and lactic acid producing bacteria, or alternatively using two separate vaccine compositions, one composition vaccinating against *Clostridium* spp. and the other composition vaccinating against lactic acid producing bacteria. Alternatively, the two separate vaccine compositions may be administered sequentially.

According to another form of the invention, the active agents may be used together.

Compositions and Routes of Administration

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered orally by inclusion in feed. The antibiotics may be fed as powders or suspended in water, included in pellets as well as being fed in premixes.

In one embodiment, the antibiotic is presented in a particulate form which is able to withstand the enzymatic digestion of the upper alimentary canal and enhances its uptake into the caecum.

Administration may be systemic, regional or local. The particular route of administration to be used in any given circumstance will depend on a number of factors, including the nature of the condition to be treated, the severity and extent of the condition, the required dosage of the particular antibiotic to be delivered and the potential side-effects of the antibiotic.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions used in the invention may be in a form suitable for administration by drenching, or in the form of a formulation suitable for oral ingestion (such as capsules, tablets, caplets, elixirs, for example).

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

For the purposes of the present invention the antibiotics may be administered to animals as compositions either therapeutically or preventively. In a therapeutic application, agents are administered to an animal already suffering from a disease, in an amount sufficient to cure or at least partially arrest the disease and its complications. The agent should provide a quantity sufficient to effectively treat the animal.

Generally, the antibiotic is administered regularly throughout the period the animal is subjected to a high carbohydrate diet or to sugars or other fermentable compounds which are not efficiently absorbed prior or reaching the large intestine, colon and caecum.

The following are to be construed as merely illustrative examples of compositions and not as a limitation of the scope of the present invention in any way.

EXAMPLES

Example 1

Dose rate study A

The Applicant has conducted an experiment in horses showing that gradual introduction of virginiamycin over 4 days as shown below does not cause a depression in feed intake.

| | |
|---|---|
| Day 1 | 25% of complete dose |
| Day 2 | 50% of complete dose |
| Day 3 | 75% of complete dose |
| Day 4 | 100% of complete dose |

Figure 2:
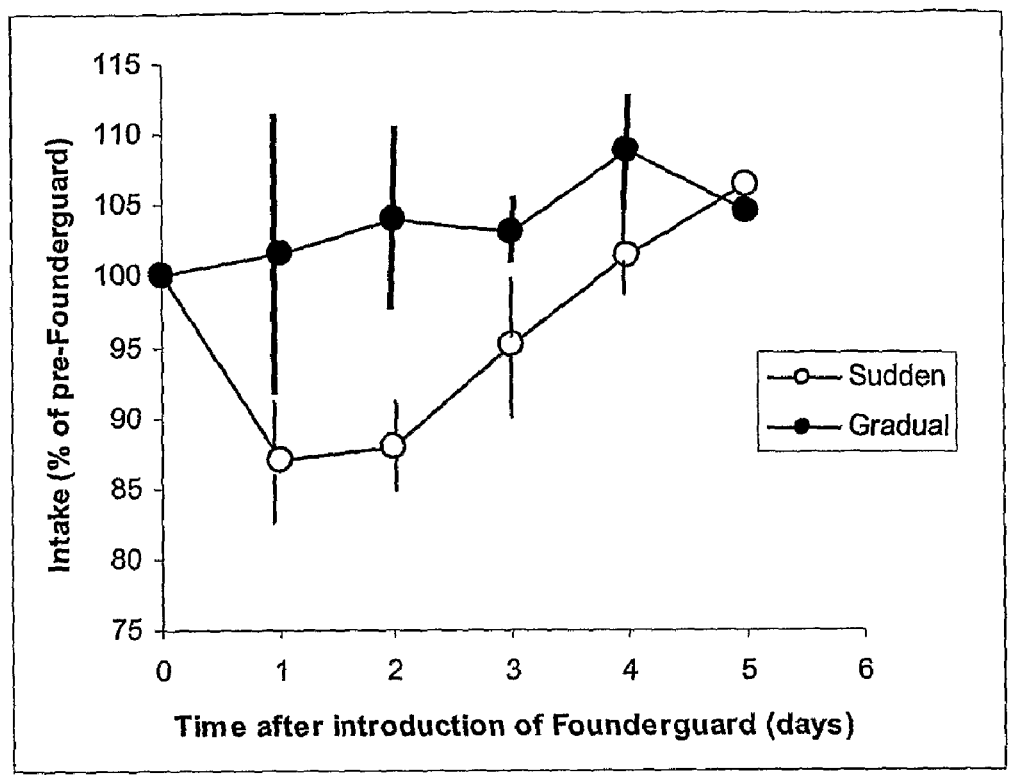
FIG. 2 shows intake of feed by horses expressed as a percentage of pre-treatment levels given virginiamycin. Horses given a 'sudden' introduction received 0.5 mg/kg body weight from days 1 to 5 whereas horses given a 'gradual' introduction received ¼, ½, and ¾ of this dose on days 1, 2 and 3 respectively before receiving the full dose of 0.5 mg/kg body weight on days 4 and 5.

The results of the experiment are summarized in FIG. 2 and show that with 'sudden' introduction of the full dose of virginiamycin (0.5 mg/kg bodyweight per day) there was a significant decrease in feed intake compared to pretreatment levels (day 0) and compared to a 'gradual' introduction as described above. This represents a major discovery with implication for horses and for production animals.

In order to achieve effective concentrations of virginiamycin to control lactic acid producing bacteria and *Clostridium* spp. throughout the digestive tract, through to the terminal colon under conditions where the risk is assessed as being high, it may be necessary to administer at least two daily doses of virginiamycin equivalent to full dose rate before animals are exposed to high levels of fermentable carbohydrate and/or *C. botulinum*.

Example 2

Dose Rate Study B

For sheep and beef cattle being fed in confinement the concentration of virginiamycin in the total mixed ration should be 5 g virginiamycin/tonne on day 1 of feeding, 10 g/tonne on day 2, 15 g/tonne on day 3 and 20 g/tonne from day 4 onwards. The amount of grain in the diet should be gradually increased as part of the introductory feeding period and should not exceed 40% of the total diet before day 5 from the start of virginiamycin and grain feeding.

Example 3

Dose Rate Effectiveness Study

Twelve horses were housed individually and fed 2.5 kg/d of a commercial horse concentrate each morning. Approximately 6 kg of medium quality lucerne hay was fed after animals had consumed the concentrate.

TABLE 1

Summary of design, animals and dose rates used to define the effective dose of virginiamycin to control the accumulation of lactic acid during fermentation of soluble carbohydrate by equine hindgut (faecal) digesta.

| HORSE | Period | Virginiamycin (mg/kg pellets) | Horse weight (kg) | Dose rate Virginiamycin (mg/d) | Dose rate Virginiamycin mg/kg live weight |
|---|---|---|---|---|---|
| 1 | 1 | 512 | 485 | 1280 | 2.639 |
| 2 | 1 | 64 | 446 | 160 | 0.359 |
| 3 | 1 | 256 | 434 | 640 | 1.475 |
| 4 | 1 | 8 | 474 | 20 | 0.042 |
| 5 | 2 | 64 | 466 | 160 | 0.343 |
| 6 | 2 | 16 | 440 | 40 | 0.091 |
| 7 | 2 | 128 | 456 | 320 | 0.702 |
| 8 | 2 | 32 | 444 | 80 | 0.180 |
| 9 | 3 | 32 | 520 | 80 | 0.154 |
| 10 | 3 | 64 | 370 | 160 | 0.432 |
| 11 | 3 | 128 | 462 | 320 | 0.693 |
| 12 | 3 | 256 | 450 | 640 | 1.422 |

The experiment was run in three periods with 4 animals in the stables during each period. Each period lasted 12 days: five days to allow adaptation to the stables and the dietary regime, and then 7 days when medicated pellets containing different concentrations of virginiamycin were fed. Faecal samples were taken on the day before feeding medicated feed and then on days 2, 4 and 6 of feeding the medicated pellets. Table 1 summarises the details of the animals and treatments.

The effectiveness of each dose rate and time on treatment was determined using an in vitro function assay to determine the amount of lactic acid produced during in vitro incubation of faecal material or samples taken from the distal colon. The fermentation of faecal material was carried out as follows. Fresh faecal material was obtained prior to the morning feed. Where warm material was available in the stable this was used, otherwise a rectal sample was obtained. A sub-sample of 150 g was mixed with an equal volume of distilled water and then strained through nylon gauze. Aliquots of supernatant were dispensed into 3 replicate tubes (4 ml/tube) and 1 ml of glucose solution (50 mg glucose/ml) was added before pricking the lid of the plastic vial with a 25 g needle and incubating for 20 to 24 hours at 37°. Following incubation the measurements of pH were made before centrifugation of a sub-sample prior to L-lactic acid analysis.

Results

Figure 3:
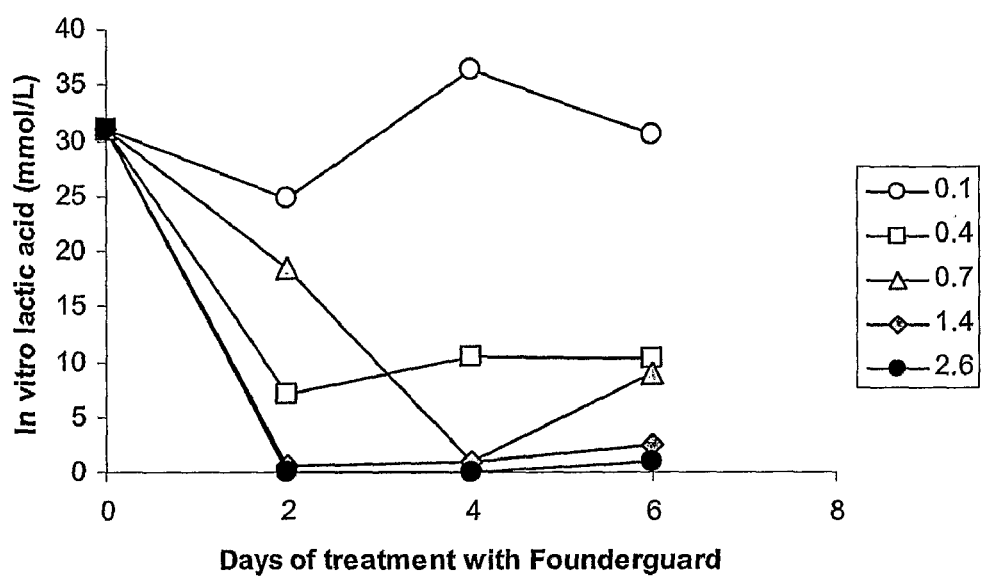
FIG. 3 shows results of in vitro function assay to measure effective dose rate of virginiamycin and time taken for oral administration to achieve effective control of lactic acid producing bacteria in the terminal colon. Dose rates in the legend refer to mg virginiamycin per kg body weight per day. Lactic acid concentrations were measured following incubation of faecal/colonic samples with excess fermentable carbohydrate.

The results of the in vitro function assay are summarised in Tables 2 and 3 and represented graphically in FIG. 3. It is relevant to note that the level of glucose used in the in vitro incubations is effectively higher than any amount of carbohydrate which could be used in vivo. In the in vitro model, no volatile fatty acids are removed from the incubation flask through "absorption".

The result of this is that the pH drops in vitro by more than it would in vivo and that a lactate-based fermentation develops more readily. It is therefore probably unrealistic to expect that lactate production can be completely controlled in this in vitro incubation model. Initially it was considered that the "baseline" in the in vitro model could be set around 10 mmol/L for an effective dose rate of virginiamycin. However, given the variable response around the 0.5 mg/kg dose rate in terms of lactic acid accumulation in the in vitro model it may be advisable to set a lower threshold for mean lactic acid concentration in determining the effective dose rate.

The summary of results in FIG. 3 shows good control of lactic acid producing bacteria in faecal/colonic digesta 48 hours after first treatment with virginiamycin at dose rates of 1.4 and 2.6 mg/kg body weight At these two high dose rates the capacity for lactic acid production remained low on days 4 and 6 as well as on day 2. Although there was a reduction in capacity for lactic acid production in samples taken on days 2, 4 and 6 from animals receiving an average of 0.4 and 0.7 mg virginiamycin/kg bodyweight per day, the response was more variable and less complete than for the higher dose rates.

Example 4

Composition for Oral Administration

A composition of an antibiotic as disclosed herein in the form of a capsule may be prepared by filling a standard two-piece hard gelatin capsule with 500 mg of the agent in powdered form, 100 mg of lactose, 35 mg of talc and 10 mg of magnesium stearate.

TABLE 2

L-lactate concentrations (mmol/L) measured following incubation of faecal samples taken from horses fed diets containing different concentrations of virginiamycin. Each value represents the mean of 3 replicates. (SEM, standard error of the mean).

| Horse | Period | Dose rate of virginiamycin mg/d | mg/kg | Day before medicated feed Mean | SEM | 2 days on medicated feed Mean | SEM | 4 days on medicated feed Mean | SEM | 6 days on medicated feed Mean | SEM |
|---|---|---|---|---|---|---|---|---|---|---|---|
| 4 | 1 | 20 | 0.042 | 25 | 0.5 | 47 | 2.7 | 47 | 2.7 | 31 | 0.4 |
| 6 | 2 | 40 | 0.091 | 15 | 0.9 | 23 | 1 | 25 | 0.7 | 24 | 0.1 |
| 8 | 2 | 80 | 0.154 | 27 | 0.5 | 5 | 0.2 | | | 44 | 0.6 |
| 9 | 3 | 80 | 0.180 | 34 | 0.4 | 4 | 0.1 | 37 | 0.9 | 29 | 0.7 |
| 2 | 1 | 160 | 0.343 | 32 | 0.1 | 17 | 0.6 | 21 | 0.2 | 12 | 0.7 |
| 5 | 2 | 160 | 0.359 | 38 | 0.5 | 0 | 0.1 | 0 | 0.1 | 0 | 0.4 |
| 11 | 3 | 160 | 0.432 | 35 | 0.1 | 4 | 0.5 | | | 19 | 0.9 |
| 10 | 3 | 320 | 0.702 | 29 | 0.6 | 1 | 0.2 | 1 | 0.1 | 15 | 0.8 |
| 12 | 3 | 320 | 0.693 | 17 | 2.5 | 36 | 2.6 | | | 3 | 0.2 |
| 7 | 2 | 640 | 1.475 | 42 | 1 | 1 | 0.1 | 1 | 0.1 | 1 | 0.2 |
| 1 | 1 | 640 | 1.422 | 48 | 0.4 | 0 | 0.1 | | | 4 | 0.5 |
| 3 | 1 | 1280 | 2.639 | 25 | 0.5 | 0 | 0.1 | 0 | 0.1 | 1 | 0.1 |

TABLE 3

The pH measured following incubation of faecal samples taken from horses fed diets containing different concentrations of virginiamycin. Each value represents the mean of 3 replicates. (SEM, standard error of the mean).

| Horse | Period | Dose rate of virginiamycin mg/d | mg/kg | Day before medicated feed Mean | SEM | 2 days on medicated feed Mean | SEM | 4 days on medicated feed Mean | SEM | 6 days on medicated feed Mean | SEM |
|---|---|---|---|---|---|---|---|---|---|---|---|
| 4 | 1 | 20 | 0.042 | 4.02 | 0.013 | 3.63 | 0.005 | 4.02 | 0.009 | 4.28 | 0.006 |
| 6 | 2 | 40 | 0.091 | 4.35 | 0.040 | 4.11 | 0.054 | 4.11 | 0.062 | | |
| 8 | 2 | 80 | 0.154 | 4.10 | 0.005 | 4.41 | 0.009 | | | 4.36 | 0.005 |
| 9 | 3 | 80 | 0.180 | 4.32 | 0.064 | 4.83 | 0.132 | 4.25 | 0.015 | | |
| 2 | 1 | 160 | 0.343 | 4.21 | 0.094 | 4.61 | 0.067 | 4.76 | 0.032 | | |
| 5 | 2 | 160 | 0.359 | 3.73 | 0.009 | 4.48 | 0.005 | 4.73 | 0.003 | 5.09 | 0.027 |
| 11 | 3 | 160 | 0.432 | 3.90 | 0.007 | 4.54 | 0.007 | | | 4.12 | 0.005 |
| 10 | 3 | 320 | 0.702 | 5.04 | 0.037 | 4.67 | 0.043 | 5.06 | 0.035 | | |
| 12 | 3 | 320 | 0.693 | 3.91 | 0.005 | 3.85 | 0.006 | | | 4.93 | 0.026 |
| 7 | 2 | 640 | 1.475 | 3.85 | 0.021 | 4.85 | 0.030 | 4.64 | 0.006 | 4.67 | 0.006 |
| 1 | 1 | 640 | 1.422 | 3.91 | 0.005 | 5.11 | 0.006 | | | 4.94 | 0.030 |
| 3 | 1 | 1280 | 2.639 | 4.06 | 0.005 | 4.43 | 0.012 | 4.71 | 0.061 | 4.59 | 0.009 |

Example 5

Composition for Oral Administration

A composition of an antibiotic as disclosed herein may be prepared in the form of a pelleted preparation containing starch and or sugars to bind the pellet in a way that it partially resists hydration and fibrous material consisting of β-linked hexose in the form of cellulose or partially lignified cellulose in order to slow down the rate of enzymic and ferementative digestion of the pelleted material. The pelleted composition also contains additives providing an attractive flavour such as molasses for equine or ruminant animals.

Example 6

Effect of Sudden or Gradual Introduction of Virginiamycin on Feed Intake

The aim of the experiment was to determine if there is a depression in feed intake when horses are first given Founderguard at the recommended dose rate of 0.5 mg virginiamycin per kg body weight per day, and whether a gradual or sudden introduction of Founderguard has different effects on feed intake during the introductory period.

Five horses of mixed ages and sexes were used in the experiment. All horses were treated against intestinal parasites prior to the Control period.

Open air feeding stalls approximately 2.5 m square were prepared with ground-level hay feeders, car tyre bucket-holders for feeding grain and a water trough shared between two stalls. Horses entered the stalls around 7.00 AM each day and were let out for exercise around 5.00 PM. Between 5.00 PM and 7.00 AM horse were in a 1.2 ha paddock with very little available grass (approximately 600 kg dry matter/ha). All horses were weighed around 5.00 PM on the third day of control period.

On entering the stalls in the morning horses were fed 1.4 kg oats in the feed bucket and soon afterwards approximately one third of their daily amount of hay. The amount of hay for each day was weighed out each morning with the aim of providing at least 20% more hay than each animal was predicted to eat. Long lucerne hay was fed as 'biscuits' from small bales into a feeder 1.5×0.5 m lined with shade-cloth and surrounded by bricks.

The remaining hay was fed in two equal amounts at around 10.00 AM and 2.00 PM. At 5.00 PM all hay remaining in and around each feeder was put into a labelled chaff bag and weighed.

All the oats offered were consumed. Intake of all feed was measured on an 'as-fed' basis. Sufficient oats was purchased and stored for the both periods. Due to limitations on storage different batches of lucerne hay were used for Period 1 and 2. While not measured objectively the quality of hay used in Period 2 was considered to be of higher quality than that used in Period 1. The effect of treatment on feed intake for each horse was calculated each day as a percentage of the mean intake for that animal during the five days of 'Control' intake measurement. Intake calculations were based on as total feed consumed: oats plus hay.

The experiment was designed as a cross-over experiment with two Periods of measurement separated by approximately five weeks for animals to 'recover' from the previous treatment regime. Each horse was randomly assigned to either sudden or gradual introduction of virginiamycin (in the form of the commercial product Founderguard) during Period 1 and then received the opposite treatment during Period 2.

Feed intake was measured for at least 5 days without Founderguard (control intake) before commencing the five day treatment period. In Period 1 the control intake was extended due to rainfall on two days. Horses were then fed just the grain in the stalls and hay ad libitum in the paddock for two days during a period of wet weather. The horses were then fed in the stalls for an additional day before commencement of the experimental period consisting of different regimes of Founderguard administration. The weights of the horses and amounts of Founderguard given on each day during Periods 1 and 2 are summarised in Table 4.

Analysis of variance was conducted (Statview 4.5) examining effects of treatment (method of Founderguard introduction) and its interaction with Period, horse and day of introduction.

A summary of Control intake for each horse is presented in Table 5 and shows that while intake varied between horses (from 2.1 to 1.0% of body weight per day) it was relatively constant for each horse. For four out of the five horses Control intake was higher during Period 2 than in Period 1.

TABLE 4

Weight of horses and the amount of Founderguard offered on each of the five days of experimental periods 1 and 2. Amounts of Founderguard are shown in g/d. Each gram of Founderguard contains 10 mg virginiamycin.

| Horse | 1 | 2 | 3 | 4 | 5 |
|---|---|---|---|---|---|
| Name | Cocoa | Fellini | Pippa | Bob | Big Red |
| Body weight (kg) | 532 | 618 | 492 | 514 | 452 |
| Founderguard (g/d) | | | | | |
| Period 1 (12-16 July) | | | | | |
| Day 1 | 26.6 | 7.7 | 24.6 | 6.4 | 22.6 |
| Day 2 | 26.6 | 15.5 | 24.6 | 12.9 | 22.6 |
| Day 3 | 26.6 | 23.2 | 24.6 | 19.3 | 22.6 |
| Day 4 | 26.6 | 30.9 | 24.6 | 25.7 | 22.6 |
| Day 5 | 26.6 | 30.9 | 24.6 | 25.7 | 22.6 |
| Period 2 (25 to 29 August) | | | | | |
| Day 1 | 6.6 | 30.9 | 6.2 | 25.7 | 5.6 |
| Day 2 | 13.3 | 30.9 | 12.3 | 25.7 | 11.3 |
| Day 3 | 19.9 | 30.9 | 18.4 | 25.7 | 16.9 |
| Day 4 | 26.6 | 30.9 | 24.6 | 25.7 | 22.6 |
| Day 5 | 26.6 | 30.9 | 24.6 | 25.7 | 22.6 |

TABLE 5

Average daily 'Control' intake and standard error during Periods 1 and 2. 'Control' intake was measured for 5 days prior to introduction of Founderguard.

| Horse | 1 | 2 | 3 | 4 | 5 |
|---|---|---|---|---|---|
| Name | Cocoa | Fellini | Pippa | Bob | Big Red |
| Body weight (kg) | 532 | 618 | 492 | 514 | 452 |
| Period 1 | | | | | |
| Average Control intake (kg/d) | 10.1 | 9.9 | 7.2 | 6.5 | 5.1 |
| Standard error of mean | 0.13 | 0.41 | 0.29 | 0.07 | 0.30 |
| Intake (% of body weight) | 1.90 | 1.60 | 1.46 | 1.02 | 1.14 |
| Period 2 | | | | | |
| Average Control intake (kg/d) | 9.8 | 12.8 | 9.1 | 8.9 | 7.7 |
| Standard error of mean | 0.52 | 0.59 | 0.24 | 0.19 | 0.28 |

TABLE 5-continued

Average daily 'Control' intake and standard error during Periods 1 and 2. 'Control' intake was measured for 5 days prior to introduction of Founderguard.

| Horse | 1 | 2 | 3 | 4 | 5 |
|---|---|---|---|---|---|
| Intake (% of body weight) | 1.83 | 2.06 | 1.85 | 1.80 | 1.56 |

The effect on feed intake associated with different methods of introducing Founderguard is shown in FIG. 2. The effect of method of Founderguard treatment had a significant ($p<0.02$) effect on feed intake during the five days following first treatment. Gradual introduction resulted in feed intake of 104.4% of the 'Control' intake and the sudden introduction 95.6% of 'Control'. The differences between treatments were greatest during the first three days of treatment (102.9 vs 90.0% for gradual and sudden introduction respectively) and this difference was highly significant ($p<0.01$). There was no significant ($p>0.15$) interaction between treatment and Period, Horse or Day of treatment.

The results indicate that sudden introduction of Founderguard at the dose rate of 0.5 mg virginiamycin per kg body weight reduced feed intake by more than 10% during the first three days of treatment. A gradual introduction of Founderguard over four days did not depress feed intake and it appears that this treatment regime will have application in situations where it is important to maintain a steady level of production or performance. It may also be important in situations where a decreased level of feed intake may have an adverse effect on digestive function and increase the risk of constipation.

The claims defining the invention are as follows:

1. A method for substantially preventing a reduction in feed intake in an equine animal which occurs when said equine animal is administered a full dose of virginiamycin, said method comprising administering to said equine animal in need of prevention of a reduction in feed intake increasing doses of virginiamycin over a specified time period prior to administering a full dose of between 0.25 mg/kg and 5 mg/kg bodyweight per day, wherein said increasing doses are each between 5% and 95% of the full dose.

2. The method of claim 1, wherein the specified time period is between 1 and 10 days.

3. The method of claim 1, wherein increasing doses of the virginiamycin comprise a first dose which is between 10% and 35% of the full dose, and a second dose which is between 40% and 60% of the full dose.

4. The method of claim 1, wherein the increasing doses of the virginiamycin comprise a first dose which is between 10% and 35% of the full dose, a second dose which is between 40% and 60% of the full dose, and a third dose which is between 65% and 85% of the full dose.

* * * * *

UNITED STATES PATENT AND TRADEMARK OFFICE
CERTIFICATE OF CORRECTION

PATENT NO. : 8,173,120 B2  Page 1 of 1
APPLICATION NO. : 12/097089
DATED : May 8, 2012
INVENTOR(S) : Rowe et al.

It is certified that error appears in the above-identified patent and that said Letters Patent is hereby corrected as shown below:

Column 4, line 31 "The fall dose" should read -- The full dose --

Signed and Sealed this
Nineteenth Day of February, 2013

Teresa Stanek Rea
*Acting Director of the United States Patent and Trademark Office*